US012661206B2

(12) United States Patent
Sekercioglu et al.

(10) Patent No.: US 12,661,206 B2
(45) Date of Patent: Jun. 23, 2026

(54) HANDHELD TOOL EXTENDER

(71) Applicant: Intuitive Surgical Operations, Inc.,
Sunnyvale, CA (US)

(72) Inventors: Salim Dogan Sekercioglu, Sunnyvale,
CA (US); Tor C. Anderson, Sunnyvale,
CA (US); Jason K. Chan, Sunnyvale,
CA (US); Benjamin G. Cohn,
Sunnyvale, CA (US); Stephan Vrudny,
Sunnyvale, CA (US); **Cynthia
Warman**, Sunnyvale, CA (US)

(73) Assignee: Intuitive Surgical Operations, Inc.,
Sunnyvale, CA (US)

( * ) Notice: Subject to any disclaimer, the term of this
patent is extended or adjusted under 35
U.S.C. 154(b) by 336 days.

(21) Appl. No.: 18/368,447

(22) Filed: Sep. 14, 2023

(65) Prior Publication Data

US 2024/0081943 A1     Mar. 14, 2024

Related U.S. Application Data

(60) Provisional application No. 63/406,495, filed on Sep.
14, 2022.

(51) Int. Cl.
A61B 90/50          (2016.01)
A61B 34/30          (2016.01)

(52) U.S. Cl.
CPC ............. A61B 90/50 (2016.02); A61B 34/30
(2016.02); *A61B 2034/301* (2016.02); *A61B*
*2217/002* (2013.01)

(58) Field of Classification Search
CPC ........ A61B 2034/301; A61B 2217/002; A61B
34/30; A61B 90/50
See application file for complete search history.

(56) References Cited

U.S. PATENT DOCUMENTS

2012/0184955 A1* 7/2012 Pivotto ................. A61B 34/30
606/41

OTHER PUBLICATIONS

Vertut, J., and Coiffet, P., "Robot Technology: Teleoperation and
Robotics Evolution and Development," English translation, Prentice-
Hall, Inc., Inglewood Cliffs, NJ, USA 1986, vol. 3A, 332 pages.

* cited by examiner

*Primary Examiner* — Scott Luan
(74) *Attorney, Agent, or Firm* — Osha Bergman Watanabe
& Burton LLP

(57)          ABSTRACT

A medical instrument includes a tool extender used to retain
and move a tool relative to a flexible elongate device. The
tool extender includes a slider that allows a user to move the
tool relative to a flexible elongate device with one hand
using a portion of the slider that is configured to be engaged
and manipulated by the user's hand or fingers. A portion of
the slider is attached to the tool shaft such that moving the
slider moves the tool relative to the tool extender and to the
flexible elongate device.

20 Claims, 11 Drawing Sheets

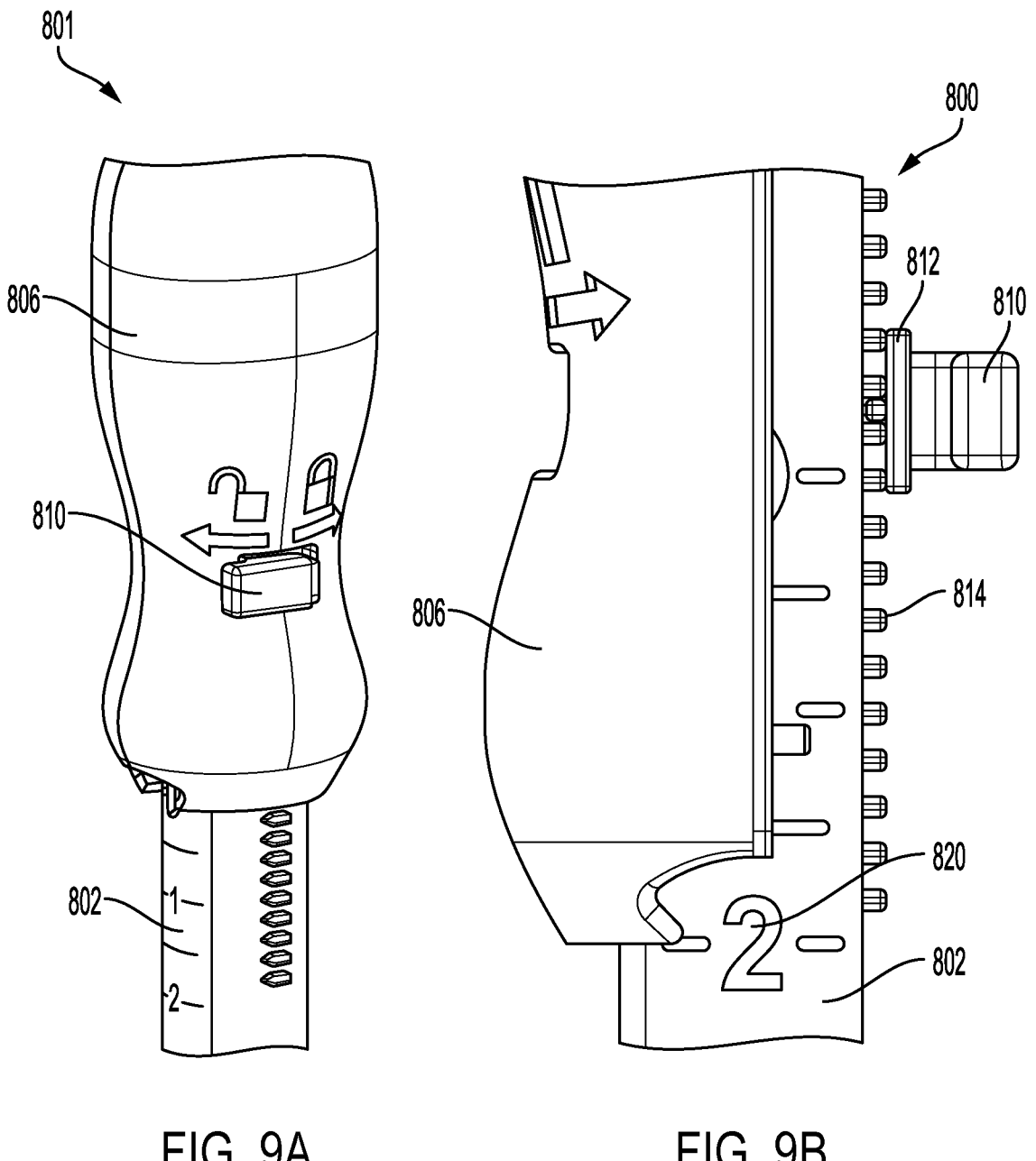
FIG. 9A                    FIG. 9B

HANDHELD TOOL EXTENDER

CROSS-REFERENCE TO RELATED APPLICATIONS

This application claims the benefit of priority under 35 U S.C. § 119(e) to U.S. Provisional Patent Application Ser. No. 63/406,495, filed on Sep. 14, 2022, which is hereby incorporated by reference herein in its entirety.

FIELD

The present disclosure is directed to systems and methods for controlling medical instruments.

BACKGROUND

Minimally invasive medical techniques are intended to reduce the amount of tissue that is damaged during medical procedures, thereby reducing patient recovery time, discomfort, and harmful side effects. Such minimally invasive techniques may be performed through natural orifices in a patient anatomy or through one or more surgical incisions. Through these natural orifices or incisions physician may insert medical instruments (including imaging surgical, diagnostic, therapeutic, or biopsy instruments) to reach a target tissue location. One such minimally invasive technique is to use a flexible and/or steerable elongate device, such as a flexible catheter, that can be inserted into anatomic passageways and navigated toward a region of interest within the patient anatomy to deliver medical instruments to the region of interest.

SUMMARY

Consistent with some embodiments, a tool extender may include an elongated housing including a channel extending through the elongated housing. The elongated housing may be configured to be attached to a tool insertion port of a flexible elongate device. The tool extender may also include a slot extending along at least a portion of a length of the elongated housing and a slider including a first portion disposed in the channel and a second portion disposed on an external surface of the elongated housing. The first portion and the second portion of the slider may be connected through the slot of the elongated housing, and the first portion of the slider may be configured to be engaged with a shaft of a tool positioned within the channel of the elongated housing.

Consistent with some embodiments, a method for controlling movement of a medical instrument may include positioning a tool in an elongated housing attached to a tool insertion port of a flexible elongate device, wherein the tool extends into a first channel extending through the flexible elongate device of a medical instrument. The method may further include retaining the tool in a slider that is slidingly disposed in a second channel extending through the elongated housing and moving the slider relative to the elongated housing while maintaining an axial position of the flexible elongate device relative to the elongated housing to move the tool relative to the flexible elongate device.

Consistent with some embodiments, a medical instrument may include a flexible elongate device including a first channel extending through a flexible elongated body of the flexible elongate device. The medical instrument may also include a tool extender operatively coupled to a tool insertion port of the flexible elongate device. The tool extender may include an elongated housing having a second channel extending through the elongated housing, a slot extending along at least a portion of a length of the elongated housing, and a slider including a first portion disposed in the second channel and a second portion disposed on an external surface of the elongated housing. The first portion and the second portion of the slider may be connected through the slot of the elongated housing, and the first portion of the slider may be configured to be engaged with a shaft of a tool positioned within the second channel of the elongated housing and the first channel of the flexible elongate device.

It should be appreciated that the foregoing concepts, and additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying figures.

In cases where the present specification and a document incorporated by reference include conflicting and/or inconsistent disclosure, the present specification shall control. If two or more documents incorporated by reference include conflicting and/or inconsistent disclosure with respect to each other, then the document having the later effective date shall control.

BRIEF DESCRIPTION OF DRAWINGS

The accompanying drawings are not intended to be drawn to scale. In the drawings, each identical or nearly identical component that is illustrated in various figures may be represented by a like numeral. For purposes of clarity, not every component may be labeled in every drawing. In the drawings:

FIG. 9A illustrates a locking mechanism of a tool extender, in accordance with embodiments of the present disclosure.

FIG. 9B illustrates the locking mechanism of the tool extender of FIG. 9A with a slider partially moved out of engagement, in accordance with embodiments of the present disclosure.

DETAILED DESCRIPTION

Figure 1:
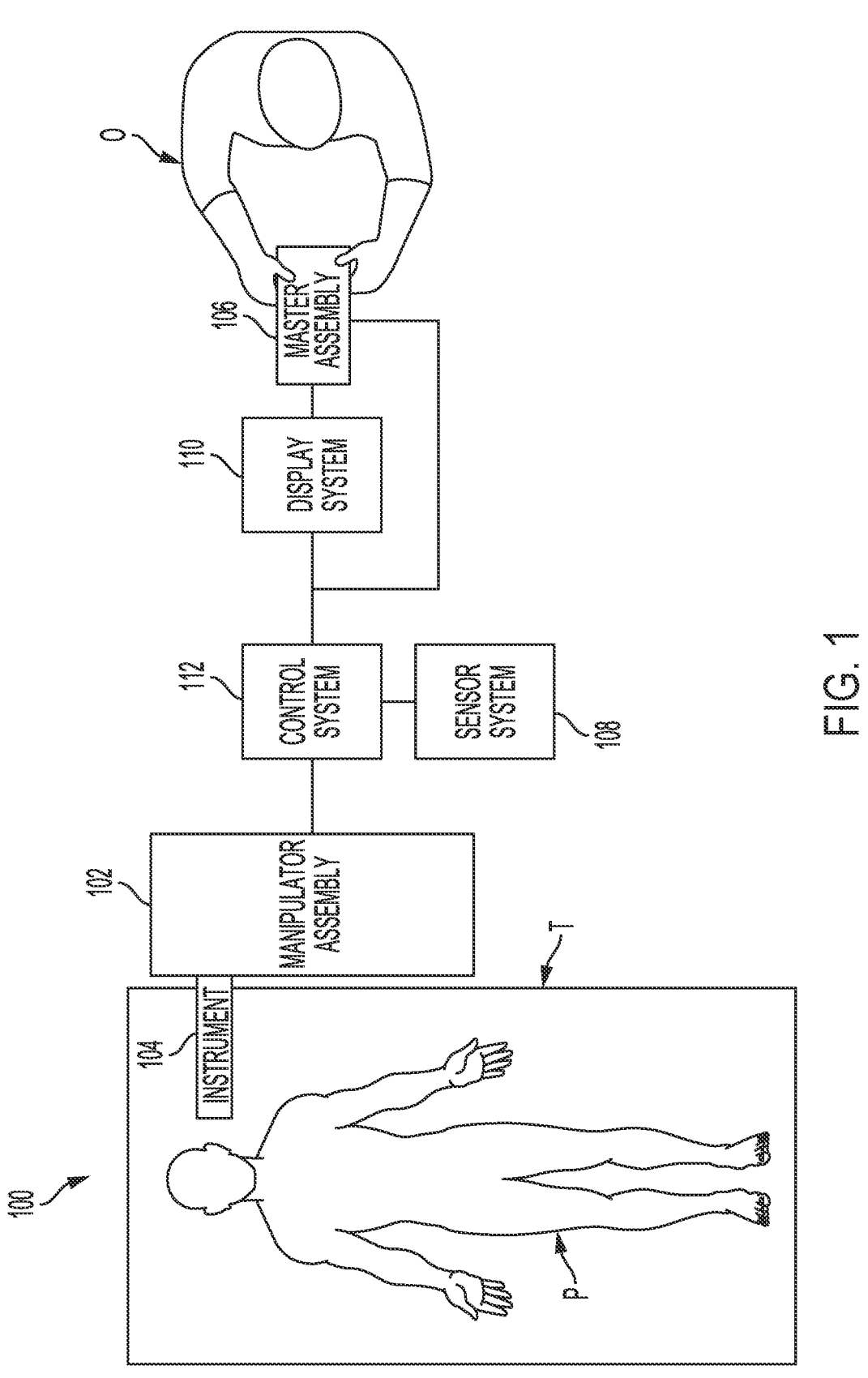
FIG. 1 is a schematic of an exemplary teleoperated medical system, in accordance with embodiments of the present disclosure.

During minimally invasive medical techniques, a flexible elongate device (e.g., catheter) may be navigated to a target site. A medical tool may then be inserted into a lumen of the flexible elongate device and navigated to a distal end of the flexible elongate device and positioned proximate to the target site. In another example, the medical tool may be within the flexible elongate device during the navigation to the target site. Once the flexible elongate device is at the target site with the medical tool inserted, the flexible elongate device is retracted while the medical tool is extended to expose the tip of the medical tool and maintain the position of the medical tool proximate to the target tissue site.

In an ablation procedure, for example, an ablation tool may be navigated through the flexible elongate device to the distal end of the flexible elongate device, or past the distal end of the flexible elongate device, such that the ablation tool is placed proximate to the target tissue while still within the lumen of the flexible elongate device. The flexible elongate device may then be retracted while the ablation tool is simultaneously extended to expose the distal end of the ablation tool and maintain the position of the ablation tool proximate to the target tissue. In another example, retraction of the flexible elongate device and extension of the ablation tool may occur at different times. Once exposed from the distal end of the flexible elongate device, the ablation tool may perform an ablation procedure on the target tissue. Retraction of the flexible elongate device during the ablation procedure exposes the energy producing portion of the ablation tool to the tissue and prevents the ablation tool from damaging the flexible elongate device. While an ablation tool is described above, similar retraction and extension procedures are performed with other types of tools as well.

The simultaneous retraction of the flexible elongate device and extension of the medical tool may be performed by an operator manually controlling the position of both the flexible elongate device and the medical tool. However, such coordination requires awkward and difficult control using two hands to perform the two different operations to maintain the tool in a desired location during retraction of the flexible elongate device. For example, one hand holds the medical tool in a desired location during separate retraction of the flexible elongate device using the other hand. Such simultaneous and precise control of the flexible elongate device and the medical tool movements is difficult.

In view of the above, designs and methods for using a medical device add the ability to manually control a tool position relative to a flexible elongate device through which the tool extends. In some embodiments, a medical instrument may include a tool extender with a slider that allows a user to move the tool relative to a flexible elongate device with one hand using a portion of the slider that is configured to be engaged and manipulated by the user's hand or fingers. Accordingly, the user's other hand is free for other tasks, such as retraction of the flexible elongate device for increased system control (e.g., either manually or via control of a robotic system that moves the flexible elongate device). In some embodiments, a portion of the slider of the tool extender is attached to a tool shaft such that the tool moves with the slider. Accordingly, moving the slider moves the tool relative to the tool extender and to the flexible elongate device. Specific embodiments of such a system are detailed further below.

In some embodiments, an elongated housing with a channel extending therethrough may attach to a tool insertion port of a flexible elongate device. The elongated housing may include a slot that extends along at least a portion of a length of the elongated housing. The elongated housing may include a coaxial slider having a first portion disposed in the channel and a second portion disposed on an external surface of the elongated housing. In some embodiments, the first portion and the second portion of the coaxial slider may be connected through the slot. In some embodiments, the slider may be configured to engage with a shaft of a tool positioned within the channel of the elongated housing. Moving the slider may move the tool relative to both the elongated housing and the associated flexible elongate device. The medical instrument may permit easy positional control of the medical tool relative to the flexible elongate device only using one hand.

The medical instruments disclosed herein may be used for medical procedures such as, but not limited to, surgery, biopsy, ablation, electroporation, illumination, irrigation, suction, imaging, or any other appropriate medical procedure. In some embodiments, medical tools used with the medical system may include biopsy, ablation, drug delivery, electroporation, surgical, imaging devices, and/or any other appropriate tool. The medical tools may be used in endoscopes, catheters, or any system with a flexible elongate device through which a medical tool may be inserted and retracted. It should be noted that any use of a catheter in some embodiments is simply for clarity, and other types of flexible elongate devices may be used. In some embodiments, a medical tool may be retained and locked into position by the tool extender using various locking techniques. Such locking techniques may include, but are not limited to compression fittings, detents, clamps, or any other appropriate holder capable of engaging with a medical tool.

In some embodiments, the slider of a tool extender may also be configured to move in various directions, including but not limited to: translation including translation in a direction aligned with a longitudinal axis of an associated portion of the flexible elongate device; rotation relative to the longitudinal axis of the flexible elongate device; combinations of the forgoing; and/or any other appropriate type of motion. The medical instrument may include markings to determine a position of the tool relative to the flexible elongate device. In some embodiments, distal ends of the tool and/or the flexible elongate device may include one or more radiopaque markers viewable on a display for a user to determine movement of the tool relative to the flexible elongate device. In some embodiments, the tool extender may include one or more measurement markings facilitate movement the tool a known distance and/or a lock to hold the tool in position relative to the flexible elongate device.

In the following description, specific details are set forth describing some embodiments consistent with the present disclosure. Numerous specific details are set forth in order to provide a thorough understanding of the embodiments. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional.

In some instances, well known methods, procedures, components, and circuits have not been described in detail so as not to unnecessarily obscure aspects of the embodiments.

This disclosure describes various instruments and portions of instruments in terms of their state in three-dimensional space. As used herein, the term "position" refers to the location of an object or a portion of an object in a three-dimensional space (e.g., three degrees of translational freedom along Cartesian x-, y-, and z-coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom). As used herein, the term "shape" refers to a set of poses, positions, or orientations measured along an object.

Turning to the figures, specific non-limiting embodiments are described in further detail. It should be understood that the various systems, components, features, and methods described relative to these embodiments may be used either individually and/or in any desired combination as the disclosure is not limited to only the specific embodiments described herein.

FIG. 1 is a simplified diagram of a medical system 100 according to some embodiments. The medical system 100 may be suitable for use in, for example, surgical, diagnostic (e.g., biopsy), or therapeutic (e.g., ablation, electroporation, etc.) procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems, general or special purpose robotic systems, general or special purpose tele operational systems, or robotic medical systems.

As shown in FIG. 1, medical system 100 may include a manipulator assembly 102 that controls the operation of a medical instrument 104 in performing various procedures on a patient P. Medical instrument 104 may extend into an internal site within the body of patient P via an opening in the body of patient P. The manipulator assembly 102 may be teleoperated, non-teleoperated, or a hybrid teleoperated and non-teleoperated assembly with one or more degrees of freedom of motion that may be motorized and/or one or more degrees of freedom of motion that may be non-motorized (e.g., manually operated). The manipulator assembly 102 may be mounted to and/or positioned near a patient table T. A master assembly 106 allows an operator O (e.g., a surgeon, a clinician, a physician, or other user) to control the manipulator assembly 102. In some examples, the master assembly 106 allows the operator O to view the procedural site or other graphical or informational displays. In some examples, the manipulator assembly 102 may be excluded from the medical system 100 and the instrument 104 may be controlled directly by the operator O. In some examples, the manipulator assembly 102 may be manually controlled by the operator O. Direct operator control may include various handles and operator interfaces for hand-held operation of the instrument 104.

The master assembly 106 may be located at a surgeon's console which is in proximity to (e.g., in the same room as) a patient table T on which patient P is located, such as at the side of the patient table T. In some examples, the master assembly 106 is remote from the patient table T, such as in in a different room or a different building from the patient table T. The master assembly 106 may include one or more control devices for controlling the manipulator assembly 102. The control devices may include any number of a variety of input devices, such as joysticks, trackballs, scroll wheels, directional pads, buttons, data gloves, trigger-guns, hand-operated controllers, voice recognition devices, motion or presence sensors, and/or the like.

The manipulator assembly 102 supports the medical instrument 104 and may include a kinematic structure of links that provide a set-up structure. The links may include one or more non-servo controlled links (e.g., one or more links that may be manually positioned and locked in place) and/or one or more servo controlled links (e.g., one or more links that may be controlled in response to commands, such as from a control system 112). The manipulator assembly 102 may include a plurality of actuators (e.g., motors) that drive inputs on the medical instrument 104 in response to commands, such as from the control system 112. The actuators may include drive systems that move the medical instrument 104 in various ways when coupled to the medical instrument 104. For example, one or more actuators may advance medical instrument 104 into a naturally or surgically created anatomic orifice. Actuators may control articulation of the medical instrument 104, such as by moving the distal end (or any other portion) of medical instrument 104 in multiple degrees of freedom. These degrees of freedom may include three degrees of linear motion (e.g., linear motion along the X, Y, Z Cartesian axes) and in three degrees of rotational motion (e.g., rotation about the X, Y, Z Cartesian axes). One or more actuators may control rotation of the medical instrument about a longitudinal axis. Actuators can also be used to move an articulable end effector of medical instrument 104, such as for grasping tissue in the jaws of a biopsy device and/or the like, or may be used to move or otherwise control tools (e.g., imaging tools, ablation tools, biopsy tools, electroporation tools, etc.) that are inserted within the medical instrument 104.

The medical system 100 may include a sensor system 108 with one or more sub-systems for receiving information about the manipulator assembly 102 and/or the medical instrument 104. Such sub-systems may include a position sensor system (e.g., that uses electromagnetic (EM) sensors or other types of sensors that detect position or location); a shape sensor system for determining the position, orientation, speed, velocity, pose, and/or shape of a distal end and/or of one or more segments along a flexible body of the medical instrument 104; a visualization system (e.g., using a color imaging device, an infrared imaging device, an ultrasound imaging device, an x-ray imaging device, a fluoroscopic imaging device, a computed tomography (CT) imaging device, a magnetic resonance imaging (MRI) imaging device, or some other type of imaging device) for capturing images, such as from the distal end of medical instrument 104 or from some other location; and/or actuator position sensors such as resolvers, encoders, potentiometers, and the like that describe the rotation and/or orientation of the actuators controlling the medical instrument 104.

The medical system 100 may include a display system 110 for displaying an image or representation of the procedural site and the medical instrument 104. Display system 110 and master assembly 106 may be oriented so physician O can control medical instrument 104 and master assembly 106 with the perception of telepresence.

In some embodiments, the medical instrument 104 may include a visualization system, which may include an image capture assembly that records a concurrent or real-time image of a procedural site and provides the image to the operator O through one or more displays of display system 110. The image capture assembly may include various types of imaging devices. The concurrent image may be, for example, a two-dimensional image or a three-dimensional image captured by an endoscope positioned within the anatomical procedural site. In some examples, the visualization system may include endoscopic components that may be integrally or removably coupled to medical instrument 104. Additionally or alternatively, a separate endoscope, attached to a separate manipulator assembly, may be used with medical instrument 104 to image the procedural site. The visualization system may be implemented as hardware, firmware, software or a combination thereof which interact with or are otherwise executed by one or more computer processors, such as of the control system 112.

Display system 110 may also display an image of the procedural site and medical instruments, which may be captured by the visualization system. In some examples, the medical system 100 provides a perception of telepresence to the operator O. For example, images captured by an imaging device at a distal portion of the medical instrument 104 may be presented by the display system 110 to provide the perception of being at the distal portion of the medical instrument 104 to the operator O. The input to the master assembly 106 provided by the operator O may move the distal portion of the medical instrument 104 in a manner that corresponds with the nature of the input (e.g., distal tip turns right when a trackball is rolled to the right) and results in corresponding change to the perspective of the images captured by the imaging device at the distal portion of the medical instrument 104. As such, the perception of telepresence for the operator O is maintained as the medical instrument 104 is moved using the master assembly 106. The operator O can manipulate the medical instrument 104 and hand controls of the master assembly 106 as if viewing the workspace in substantially true presence, simulating the experience of an operator that is physically manipulating the medical instrument 104 from within the patient anatomy.

In some examples, the display system 110 may present virtual images of a procedural site that are created using image data recorded pre-operatively (e.g., prior to the procedure performed by the medical instrument system 200) or intra-operatively (e.g., concurrent with the procedure performed by the medical instrument system 200), such as image data created using computed tomography (CT), magnetic resonance imaging (MRI), positron emission tomography (PET), fluoroscopy, thermography, ultrasound, optical coherence tomography (OCT), thermal imaging, impedance imaging, laser imaging, nanotube X-ray imaging, and/or the like. The virtual images may include two-dimensional, three-dimensional, or higher-dimensional (e.g., including, for example, time based or velocity-based information) images. In some examples, one or more models are created from pre-operative or intra-operative image data sets and the virtual images are generated using the one or more models.

In some examples, for purposes of imaged guided medical procedures, display system 110 may display a virtual image that is generated based on tracking the location of medical instrument 104. For example, the tracked location of the medical instrument 104 may be registered (e.g., dynamically referenced) with the model generated using the pre-operative or intra-operative images, with different portions of the model correspond with different locations of the patient anatomy. As the medical instrument 104 moves through the patient anatomy, the registration is used to determine portions of the model corresponding with the location and/or perspective of the medical instrument 104 and virtual images are generated using the determined portions of the model. This may be done to present the operator O with virtual images of the internal procedural site from viewpoints of medical instrument 104 that correspond with the tracked locations of the medical instrument 104.

The medical system 100 may also include the control system 112, which may include processing circuitry that implements the some or all of the methods or functionality discussed herein. The control system 112 may include at least one memory and at least one processor for controlling the operations of the manipulator assembly 102, the medical instrument 104, the master assembly 106, the sensor system 108, and/or the display system 110. Control system 112 may include instructions (e.g., a non-transitory machine-readable medium storing the instructions) that when executed by the at least one processor, configures the one or more processors to implement some or all of the methods or functionality discussed herein. While the control system 112 is shown as a single block in FIG. 1, the control system 112 may include two or more separate data processing circuits with one portion of the processing being performed at the manipulator assembly 102, another portion of the processing being performed at the master assembly 106, and/or the like. In some examples, the control system 112 may include other types of processing circuitry, such as application-specific integrated circuits (ASICs) and/or field-programmable gate array (FPGAs). The control system 112 may be implemented using hardware, firmware, software, or a combination thereof.

In some examples, the control system 112 may receive feedback from the medical instrument 104, such as force and/or torque feedback. Responsive to the feedback, the control system 112 may transmit signals to the master assembly 106. In some examples, the control system 112 may transmit signals instructing one or more actuators of the manipulator assembly 102 to move the medical instrument 104. In some examples, the control system 112 may transmit informational displays regarding the feedback to the display system 110 for presentation or perform other types of actions based on the feedback.

The control system 112 may include a virtual visualization system to provide navigation assistance to operator O when controlling the medical instrument 104 during an image-guided medical procedure. Virtual navigation using the virtual visualization system may be based upon an acquired pre-operative or intra-operative dataset of anatomic passageways of the patient P. The control system 112 or a separate computing device may convert the recorded images, using programmed instructions alone or in combination with operator inputs, into a model of the patient anatomy. The model may include a segmented two-dimensional or three-dimensional composite representation of a partial or an entire anatomic organ or anatomic region. An image data set may be associated with the composite representation. The virtual visualization system may obtain sensor data from the sensor system 108 that is used to compute an (e.g., approximate) location of the medical instrument 104 with respect to the anatomy of patient P. The sensor system 108 may be used to register and display the medical instrument 104 together with the pre-operatively or intra-operatively recorded images. For example, PCT Publication WO 2016/191298 (published Dec. 1, 2016 and titled "Systems and Methods of Registration for Image Guided Surgery"), which is incorporated by reference herein in its entirety, discloses example systems.

During a virtual navigation procedure, the sensor system 108 may be used to compute the (e.g., approximate) location of the medical instrument 104 with respect to the anatomy of patient P. The location can be used to produce both macro-level (e.g., external) tracking images of the anatomy of patient P and virtual internal images of the anatomy of patient P. The system may include one or more electromagnetic (EM) sensors, fiber optic sensors, and/or other sensors to register and display a medical instrument together with pre-operatively recorded medical images. For example, U.S. Pat. No. 8,900,131 (filed May 13, 2011 and titled "Medical System Providing Dynamic Registration of a Model of an Anatomic Structure for Image-Guided Surgery"), which is incorporated by reference herein in its entirety, discloses example systems.

Medical system 100 may further include operations and support systems (not shown) such as illumination systems, steering control systems, irrigation systems, and/or suction systems. In some embodiments, the medical system 100 may include more than one manipulator assembly and/or more than one master assembly. The exact number of manipulator assemblies may depend on the medical procedure and space constraints within the procedural room, among other factors. Multiple master assemblies may be co-located or they may be positioned in separate locations. Multiple master assemblies may allow more than one operator to control one or more manipulator assemblies in various combinations.

Figures 2A, 2B:
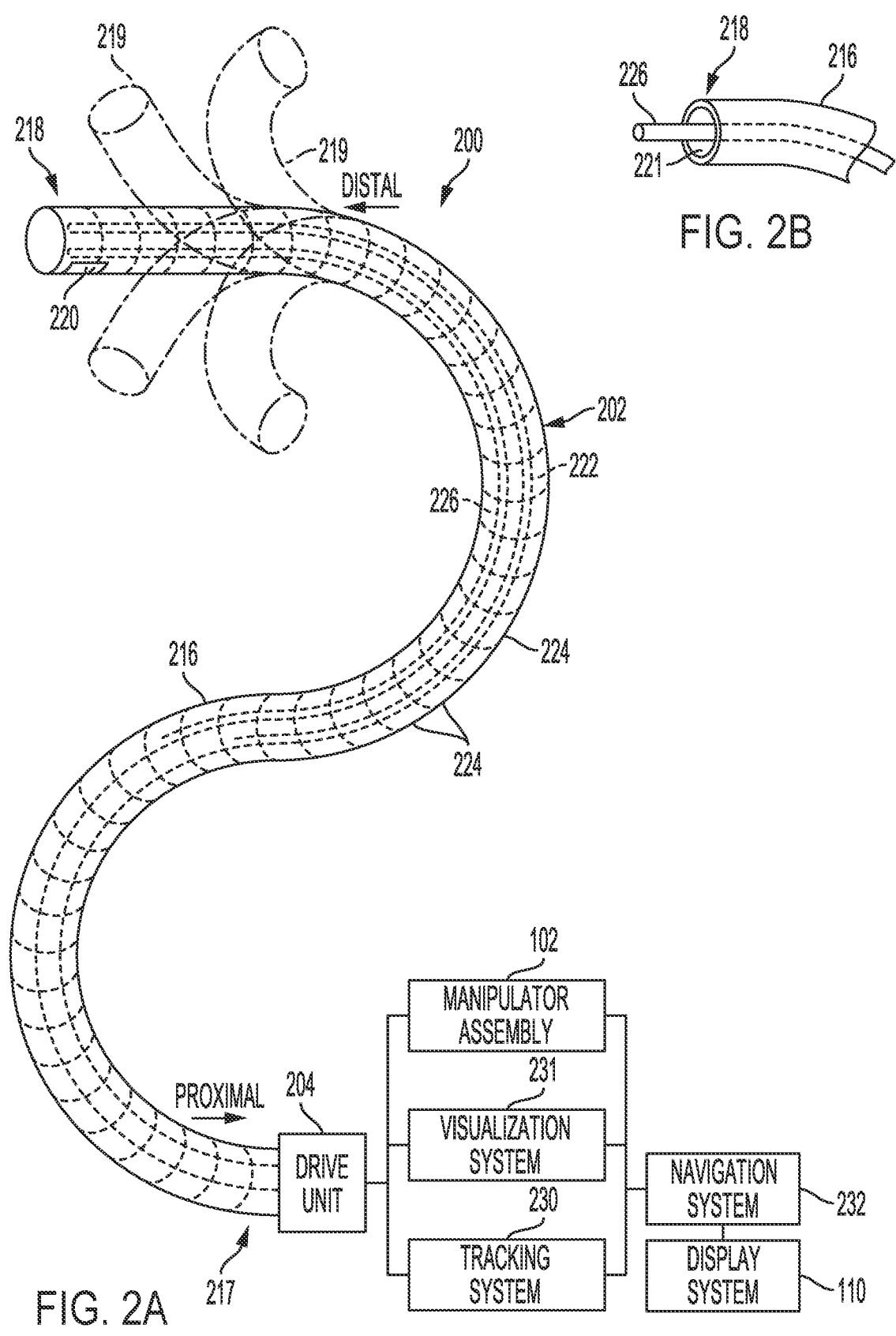
FIG. 2A illustrates a medical instrument system, in accordance with embodiments of the present disclosure.
FIG. 2B illustrates a distal end portion of a medical instrument system, in accordance with embodiments of the present disclosure.

FIG. 2A is a simplified diagram of a medical instrument system 200 according to some embodiments. The medical instrument system 200 includes a flexible elongate device 202 (also referred to as elongate device 202), a drive unit 204, and a medical tool 226 that collectively is an example of a medical instrument 104 of a medical system 100. The medical system 100 may be a teleoperated system, a non-teleoperated system, or a hybrid teleoperated and non-teleoperated system, as explained with reference to FIG. 1. A visualization system 231, tracking system 230, and navigation system 232 are also shown in FIG. 2A and are example components of the control system 112 of the medical system 100. In some examples, the medical instrument system 200 may be used for non-teleoperational exploratory procedures or in procedures involving traditional manually operated medical instruments, such as endoscopy. The medical instrument system 200 may be used to gather (e.g., measure) a set of data points corresponding to locations within anatomic passageways of a patient, such as patient P.

The elongate device 202 is coupled to the drive unit 204. The elongate device 202 includes a channel 221 through which the medical tool 226 may be inserted. The elongate device 202 navigates within patient anatomy to deliver the medical tool 226 to a procedural site. The elongate device 202 includes a flexible body 216 having a proximal end 217 and a distal end 218. In some examples, the flexible body 216 may have an approximately 3 mm outer diameter. Other flexible body outer diameters may be larger or smaller.

Medical instrument system 200 may include the tracking system 230 for determining the position, orientation, speed, velocity, pose, and/or shape of the flexible body 216 at the distal end 218 and/or of one or more segments 224 along flexible body 216, as will be described in further detail below. The tracking system 230 may include one or more sensors and/or imaging devices. The flexible body 216, such as the length between the distal end 218 and the proximal end 217, may include multiple segments 224. The tracking system 230 may be implemented using hardware, firmware, software, or a combination thereof. In some examples, the tracking system 230 is part of control system 112 shown in FIG. 1.

Tracking system 230 may track the distal end 218 and/or one or more of the segments 224 of the flexible body 216 using a shape sensor 222. The shape sensor 222 may include an optical fiber aligned with the flexible body 216 (e.g., provided within an interior channel of the flexibly body 216 or mounted externally along the flexible body 216). In some examples, the optical fiber may have a diameter of approximately 200 μm. In other examples, the diameter may be larger or smaller. The optical fiber of the shape sensor 222 may form a fiber optic bend sensor for determining the shape of flexible body 216. Optical fibers including Fiber Bragg Gratings (FBGs) may be used to provide strain measurements in structures in one or more dimensions. Various systems and methods for monitoring the shape and relative position of an optical fiber in three dimensions, which may be applicable in some embodiments, are described in U.S. Patent Application Publication No. 2006/0013523 (filed Jul. 13, 2005 and titled "Fiber optic position and shape sensing device and method relating thereto"); U.S. Pat. No. 7,772,541 (filed on Mar. 12, 2008 and titled "Fiber Optic Position and/or Shape Sensing Based on Rayleigh Scatter"); and U.S. Pat. No. 8,773,650 (filed on Sep. 2, 2010 and titled "Optical Position and/or Shape Sensing"), which are all incorporated by reference herein in their entireties. Sensors in some embodiments may employ other suitable strain sensing techniques, such as Rayleigh scattering, Raman scattering, Brillouin scattering, and Fluorescence scattering.

In some examples, the shape of the flexible body 216 may be determined using other techniques. For example, a history of the position and/or pose of the distal end 218 of the flexible body 216 can be used to reconstruct the shape of flexible body 216 over an interval of time (e.g., as the flexible body 216 is advanced or retracted within a patient anatomy). In some examples, the tracking system 230 may alternatively and/or additionally track the distal end 218 of the flexible body 216 using a position sensor system 220. Position sensor system 220 may be a component of an EM sensor system with the position sensor system 220 including one or more position sensors. Although the position sensor system 220 is shown as being near the distal end 218 of the flexible body 216 to track the distal end 218, the number and location of the position sensors of the position sensor system 220 may vary to track different regions along the flexible body 216. In one example, the position sensors include conductive coils that may be subjected to an externally generated electromagnetic field. Each coil of position sensor system 220 may produce an induced electrical signal having characteristics that depend on the position and orientation of the coil relative to the externally generated electromagnetic field. The position sensor system 220 may measure one or more position coordinates and/or one or more orientation angles associated with one or more portions of flexible body 216. In some examples, the position sensor system 220 may be configured and positioned to measure six degrees of freedom, e.g., three position coordinates X, Y, Z and three orientation angles indicating pitch, yaw, and roll of a base point. In some examples, the position sensor system 220 may be configured and positioned to measure five degrees of freedom, e.g., three position coordinates X, Y, Z and two orientation angles indicating pitch and yaw of a base point. Further description of a position sensor system, which may be applicable in some embodiments, is provided in U.S. Pat. No. 6,380,732 (filed Aug. 11, 1999 and titled "Six-Degree of Freedom Tracking System Having a Passive Transponder on the Object Being Tracked"), which is incorporated by reference herein in its entirety.

In some embodiments, the tracking system 230 may alternately and/or additionally rely on a collection of pose, position, and/or orientation data stored for a point of an elongate device 202 and/or medical tool 226 captured during one or more cycles of alternating motion, such as breathing. This stored data may be used to develop shape information about the flexible body 216. In some examples, a series of position sensors (not shown), such as EM sensors like the sensors in position sensor 220 or some other type of position sensors may be positioned along the flexible body 216 and used for shape sensing. In some examples, a history of data from one or more of these position sensors taken during a procedure may be used to represent the shape of elongate device 202, particularly if an anatomic passageway is generally static.

FIG. 2B is a simplified diagram of the medical tool 226 within the elongate device 202 according to some embodiments. The flexible body 216 of the elongate device 202 may include the channel 221 sized and shaped to receive the medical tool 226. In some embodiments, the medical tool 226 may be used for procedures such as diagnostics, imaging, surgery, biopsy, ablation, illumination, irrigation, suction, electroporation, etc. Medical tool 226 can be deployed through channel 221 of flexible body 216 and operated at a procedural site within the anatomy. Medical instrument 226 may be, for example, an image capture probe, a biopsy tool (e.g., a needle, grasper, brush, etc.), an ablation tool (e.g., a laser ablation tool, radio frequency (RF) ablation tool, cryoablation tool, thermal ablation tool, heated liquid ablation tool, etc.), an electroporation tool, and/or another surgical, diagnostic, or therapeutic tool. In some examples, the medical tool 226 may include an end effector having a single working member such as a scalpel, a blunt blade, an optical fiber, an electrode, and/or the like. Other end types of end effectors may include, for example, forceps, graspers, scissors, staplers, clip appliers, and/or the like. Other end effectors may further include electrically activated end effectors such as electrosurgical electrodes, transducers, sensors, and/or the like.

The medical tool 226 may be a biopsy tool used to remove sample tissue or a sampling of cells from a target anatomic location. In some examples, the biopsy tool is a flexible needle. The biopsy tool may further include a sheath that can surround the flexible needle to protect the needle and interior surface of the channel 221 when the biopsy tool is within the channel 221. The medical tool 226 may be an image capture probe that includes a distal portion with a stereoscopic or monoscopic camera that may be placed at or near the distal end 218 of flexible body 216 for capturing images (e.g., still or video images). The captured images may be processed by the visualization system 231 for display and/or provided to the tracking system 230 to support tracking of the distal end 218 of the flexible body 216 and/or one or more of the segments 224 of the flexible body 216. The image capture probe may include a cable for transmitting the captured image data that is coupled to an imaging device at the distal portion of the image capture probe. In some examples, the image capture probe may include a fiber-optic bundle, such as a fiberscope, that couples to a more proximal imaging device of the visualization system 231. The image capture probe may be single-spectral or multi-spectral, for example, capturing image data in one or more of the visible, near-infrared, infrared, and/or ultraviolet spectrums. The image capture probe may also include one or more light emitters that provide illumination to facilitate image capture. In some examples, the image capture probe may use ultrasound, x-ray, fluoroscopy, CT, MRI, or other types of imaging technology.

In some examples, the image capture probe is inserted within the flexible body 216 of the elongate device 202 to facilitate visual navigation of the elongate device 202 to a procedural site and then is replaced within the flexible body 216 with another type of medical tool 226 that performs the procedure. In some examples, the image capture probe may be within the flexible body 216 of the elongate device 202 along with another type of medical tool 226 to facilitate simultaneous image capture and tissue intervention, such as within the same channel 221 or in separate channels. A medical tool 226 may be advanced from the opening of the channel 221 to perform the procedure (or some other functionality) and then retracted back into the channel 221 when the procedure is complete. The medical tool 226 may be removed from the proximal end 217 of the flexible body 216 or from another optional instrument port (not shown) along flexible body 216.

In some examples, the elongate device 202 may include integrated imaging capability rather than utilize a removable image capture probe. For example, the imaging device (or fiber-optic bundle) and the light emitters may be located at the distal end 218 of the elongate device 202. The flexible body 215 may include one or more dedicated channels that carry the cable(s) and/or optical fiber(s) between the distal end 218 and the visualization system 231. Here, the medical instrument system 200 can perform simultaneous imaging and tool operations.

In some examples, the medical tool 226 is capable of controllable articulation. The medical tool 226 may house cables (which may also be referred to as pull wires), linkages, or other actuation controls (not shown) that extend between its proximal and distal ends to controllably bend the distal end of medical tool 226, such as discussed herein for the flexible elongate device 202. The medical tool 226 may be coupled to a drive unit 204 and the manipulator assembly 102. In these examples, the elongate device 202 may be excluded from the medical instrument system 200 or may be a flexible device that does not have controllable articulation. Steerable instruments or tools, applicable in some embodiments, are further described in detail in U.S. Pat. No. 7,316,681 (filed on Oct. 4, 2005 and titled "Articulated Surgical Instrument for Performing Minimally Invasive Surgery with Enhanced Dexterity and Sensitivity") and U.S. Pat. No. 9,259,274 (filed Sep. 30, 2008 and titled "Passive Preload and Capstan Drive for Surgical Instruments"), which are incorporated by reference herein in their entireties.

The flexible body 216 of the elongate device 202 may also or alternatively house cables, linkages, or other steering controls (not shown) that extend between the drive unit 204 and the distal end 218 to controllably bend the distal end 218 as shown, for example, by broken dashed line depictions 219 of the distal end 218 in FIG. 2A. In some examples, at least four cables are used to provide independent up-down steering to control a pitch of the distal end 218 and left-right steering to control a yaw of the distal end 281. In these examples, the flexible elongate device 202 may be a steerable catheter. Examples of steerable catheters, applicable in some embodiments, are described in detail in PCT Publication WO 2019/018736 (published Jan. 24, 2019 and titled "Flexible Elongate Device Systems and Methods"), which is incorporated by reference herein in its entirety.

In embodiments where the elongate device 202 and/or medical tool 226 are actuated by a teleoperational assembly (e.g., the manipulator assembly 102), the drive unit 204 may include drive inputs that removably couple to and receive power from drive elements, such as actuators, of the teleoperational assembly. In some examples, the elongate device 202 and/or medical tool 226 may include gripping features, manual actuators, or other components for manually controlling the motion of the elongate device 202 and/or medical tool 226. The elongate device 202 may be steerable or, alternatively, the elongate device 202 may be non-steerable with no integrated mechanism for operator control of the bending of distal end 218. In some examples, one or more channels 221 (which may also be referred to as lumens), through which medical tools 226 can be deployed and used at a target anatomical location, may be defined by the interior walls of the flexible body 216 of the elongate device 202.

In some examples, the medical instrument system 200 (e.g., the elongate device 202 or medical tool 226) may include a flexible bronchial instrument, such as a bronchoscope or bronchial catheter, for use in examination, diagnosis, biopsy, and/or treatment of a lung. The medical instrument system 200 may also be suited for navigation and treatment of other tissues, via natural or surgically created connected passageways, in any of a variety of anatomic systems, including the colon, the intestines, the kidneys and kidney calices, the brain, the heart, the circulatory system including vasculature, and/or the like.

The information from the tracking system 230 may be sent to the navigation system 232, where the information may be combined with information from the visualization system 231 and/or pre-operatively obtained models to provide the physician, clinician, surgeon, or other operator with real-time position information. In some examples, the real-time position information may be displayed on the display system 110 for use in the control of the medical instrument system 200. In some examples, the navigation system 232 may utilize the position information as feedback for positioning medical instrument system 200. Various systems for using fiber optic sensors to register and display a surgical instrument with surgical images, applicable in some embodiments, are provided in U.S. Pat. No. 8,900,131 (filed May 13, 2011 and titled "Medical System Providing Dynamic Registration of a Model of an Anatomic Structure for Image-Guided Surgery"), which is incorporated by reference herein in its entirety.

Figure 3A:
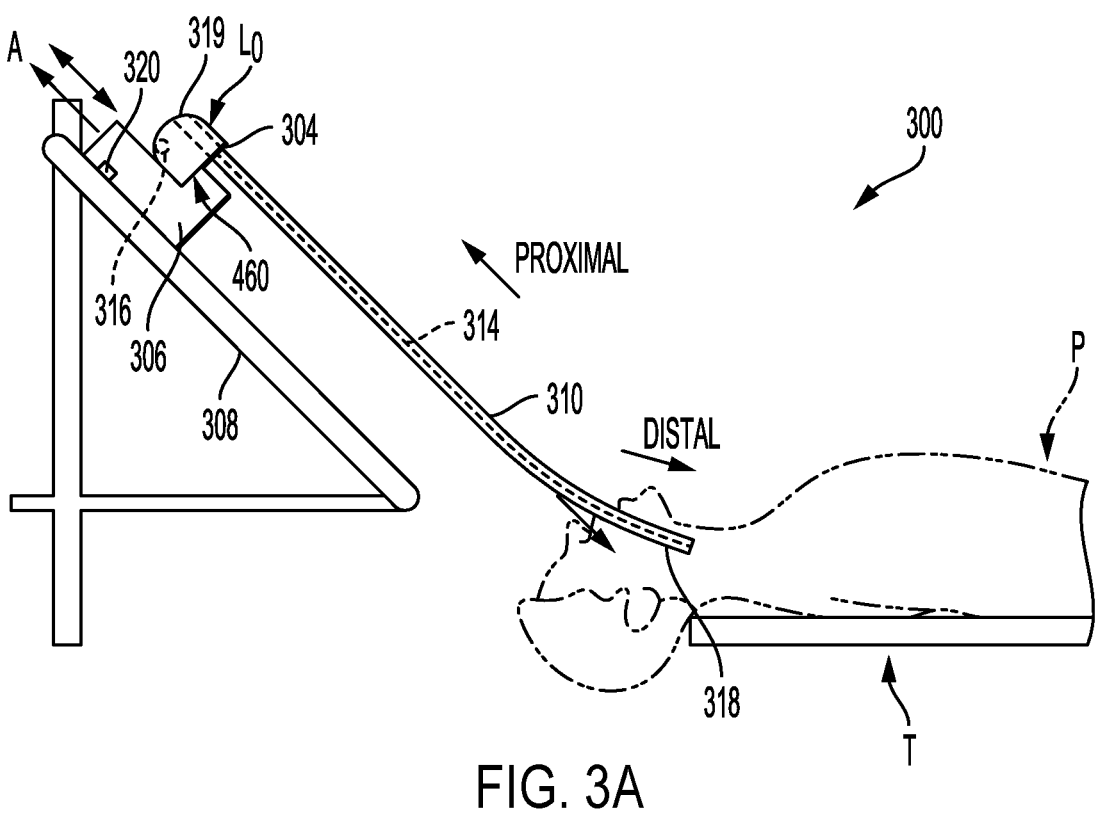
FIGS. 3A and 3B illustrate side views of a medical instrument mounted on an insertion assembly and positioned to treat a patient, in accordance with embodiments of the present disclosure.
Figure 3B:
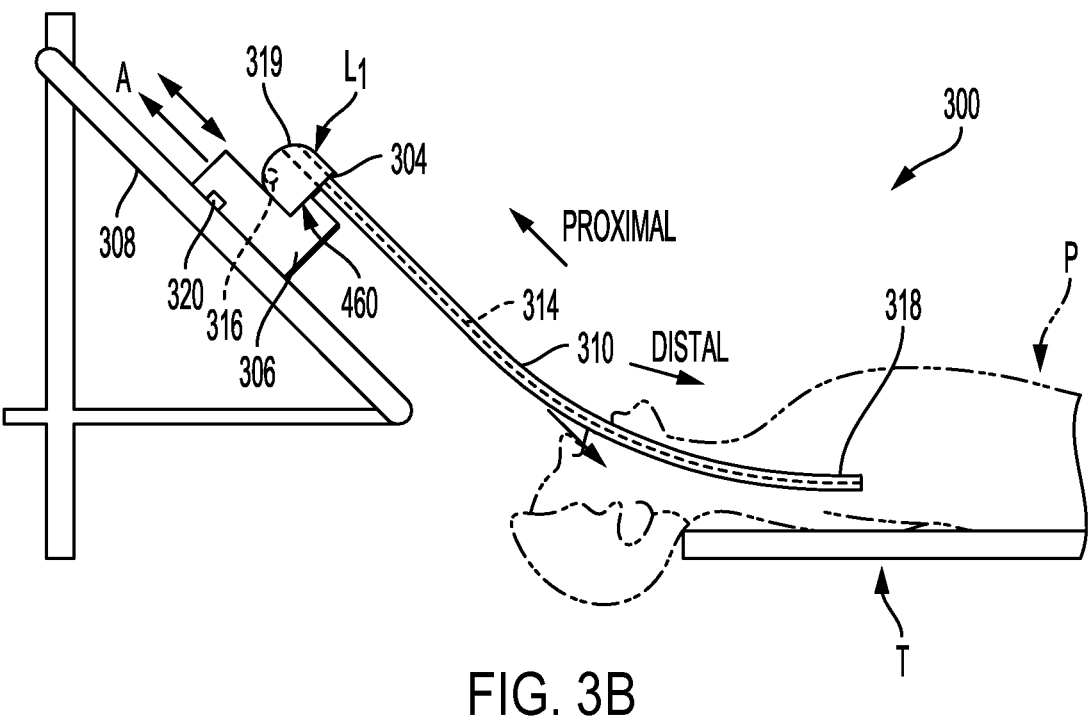

FIGS. 3A and 3B are simplified diagrams of side views of a medical instrument mounted on an insertion assembly and position to treat a patient according to some embodiments. As shown in FIGS. 3A and 3B, an environment 300 includes a patient P positioned on the table T of FIG. 1. Patient P may be stationary within the surgical environment in the sense that gross patient movement is limited by sedation, restraint, and/or other means. Cyclic anatomic motion including respiration and cardiac motion of patient P may continue, unless patient is asked to hold his or her breath to temporarily suspend respiratory motion. Accordingly, in some embodiments, data may be gathered at a specific, phase in respiration, and tagged and identified with that phase. In some embodiments, the phase during which data is collected may be inferred from physiological information collected from patient P. Within environment 300, a backend mechanism 304 can be removably coupled to an instrument carriage 306. In some embodiments, the backend mechanism 304 may be formed of a housing containing operational components for cables used to provide independent up down steering to control a pitch of distal end 318 and left right steering to control a yaw of distal end 318. In addition, the backend mechanism 304 may comprise EM sensors, shape-sensors, and/or other sensor modalities and or provide connectors coupling sensing modalities to an instrument such as flexible elongate device 310.

Instrument carriage 306 can be mounted to an insertion stage 308 which is fixed within environment 300. Alternatively, insertion stage 308 may be movable but have a known location (e.g., via a tracking sensor or other tracking device) within environment 300. Instrument carriage 306 may be a component of a teleoperational manipulator or a non-teleoperational manipulator assembly (e.g., manipulator assembly 102) that controls insertion motion (i.e., motion along the A axis) and, optionally, motion of a distal end 318 of a flexible elongate device 310 in multiple directions including yaw, pitch, and roll. Instrument carriage 306 or insertion stage 308 may include actuators, such as servomotors, (not shown) that control motion of instrument carriage 306 along insertion stage 308, control motion of the distal end 318 of flexible elongate device 310 in yaw/pitch, and/or control roll motion of flexible elongate device 310 along a longitudinal axis. In some embodiments described herein, the actuators used to control movement of the elongated member attached to the carriage or other appropriate structure, may be referred to as flexible elongate device actuators.

Flexible elongate device 310 is coupled to backend mechanism 304. Backend mechanism 304 is coupled and fixed relative to instrument carriage 306. In some embodiments, an optical fiber shape sensor 314 is fixed at a proximal point 316 on backend mechanism 304. In some embodiments, proximal point 316 of optical fiber shape sensor 314 may be movable along with backend mechanism 304 but the location of proximal point 316 may be known (e.g., via a tracking sensor or other tracking device). Shape sensor 314 measures a shape from proximal point 316 to another point such as distal end 318 or a point along a distal portion of flexible elongate device 310.

A position measuring device 320 provides information about the position of backend mechanism 304 as it moves on insertion stage 308 along an insertion axis A. Position measuring device 320 may include resolvers, encoders, potentiometers, and/or other sensors that determine the rotation and/or orientation of the actuators controlling the motion of instrument carriage 306 and consequently the motion of backend mechanism 304. In some embodiments, insertion stage 308 is linear. In some embodiments, insertion stage 308 may be curved or have a combination of curved and linear sections.

FIG. 3A shows backend mechanism 304 and instrument carriage 306 in a retracted position along insertion stage 308. In this retracted position, proximal point 316 is at a position L0 on axis A. In this position along insertion stage 308 a component of the location of proximal point 316 may be set to a zero and/or another reference value to provide a base reference to describe the position of instrument carriage 306, and thus proximal point 316, on insertion stage 308. With this retracted position of backend mechanism 304 and instrument carriage 306, distal end 318 of flexible elongate device 310 may be positioned proximal to, e.g., just inside, just outside, or otherwise near an entry orifice of patient P. Also in this position, position measuring device 320 may be set to a zero and/or another reference value (e.g., 1=0). In FIG. 3B, backend mechanism 304 and instrument carriage 306 have advanced along the linear track of insertion stage 308 and distal end 318 of flexible elongate device 310 has advanced into patient P. In this advanced position, the proximal point 316 is at a position L1 on the axis A. In some examples, encoder and/or other position data from one or more actuators controlling movement of instrument carriage 306 along insertion stage 308 and/or one or more position sensors associated with instrument carriage 306 and/or insertion stage 308 is used to determine the position Lx of proximal point 316 relative to position L0. In some examples, position Lx may further be used as an indicator of the distance or insertion depth to which distal end 318 of flexible elongate device 310 is inserted into the passageways of the anatomy of patient P.

In FIG. 3A, the backend mechanism 304 includes a mounting face 460, that may define a mounting plane. A portion of the mounting face 460, referred to as an interfacing region, is disposed against the instrument carriage 306, while another portion of the mounting face 460, referred to as a non-interfacing region, protrudes outwardly beyond an edge of the instrument carriage 306. As can be seen, the flexible elongate device 310 extends from the backend mechanism 304, out of the mounting face 460, and past the instrument carriage 306.

Figure 4:
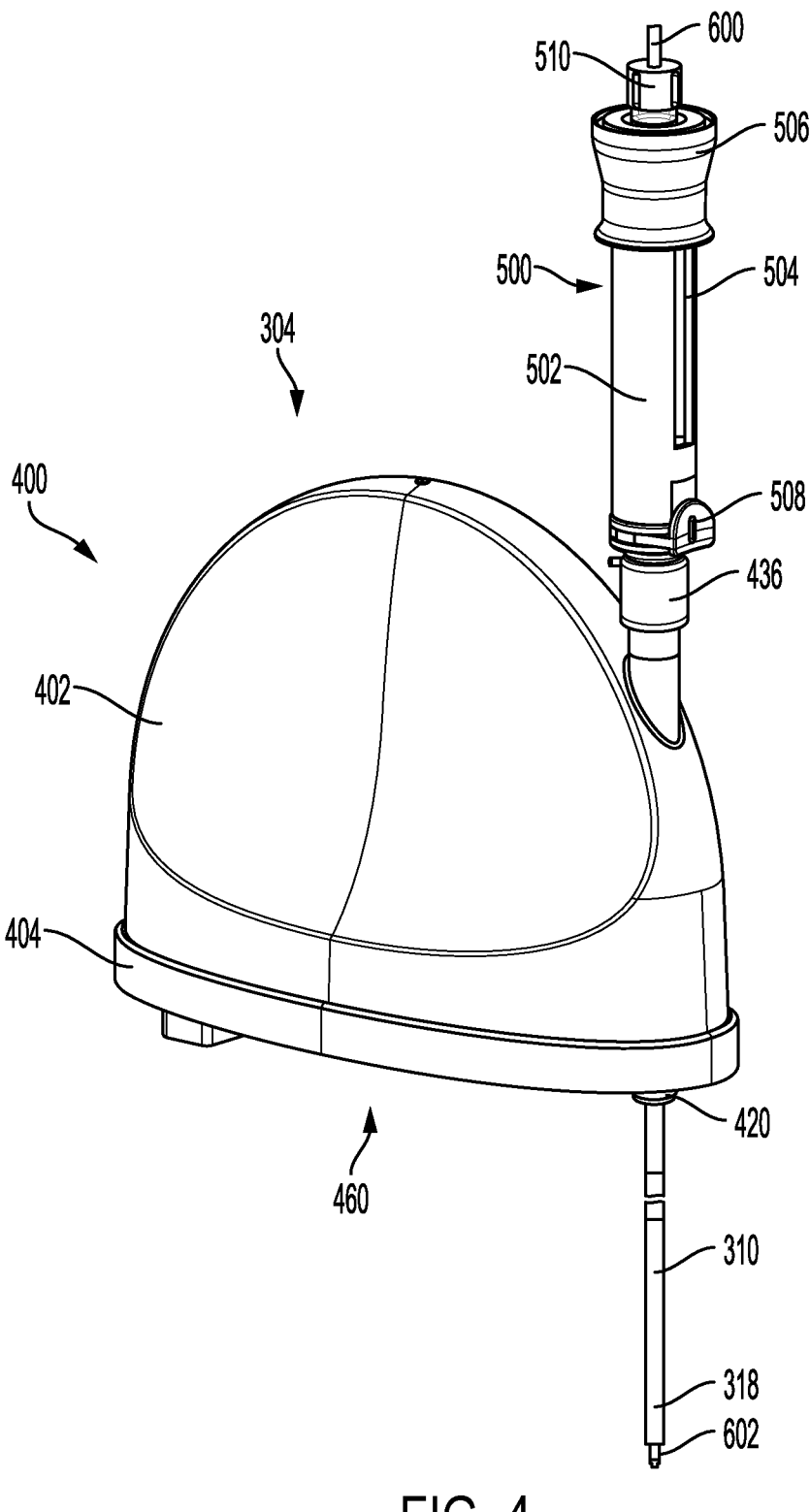
FIG. 4 illustrates a backend mechanism of a medical instrument system, in accordance with embodiments of the present disclosure.
Figure 5:
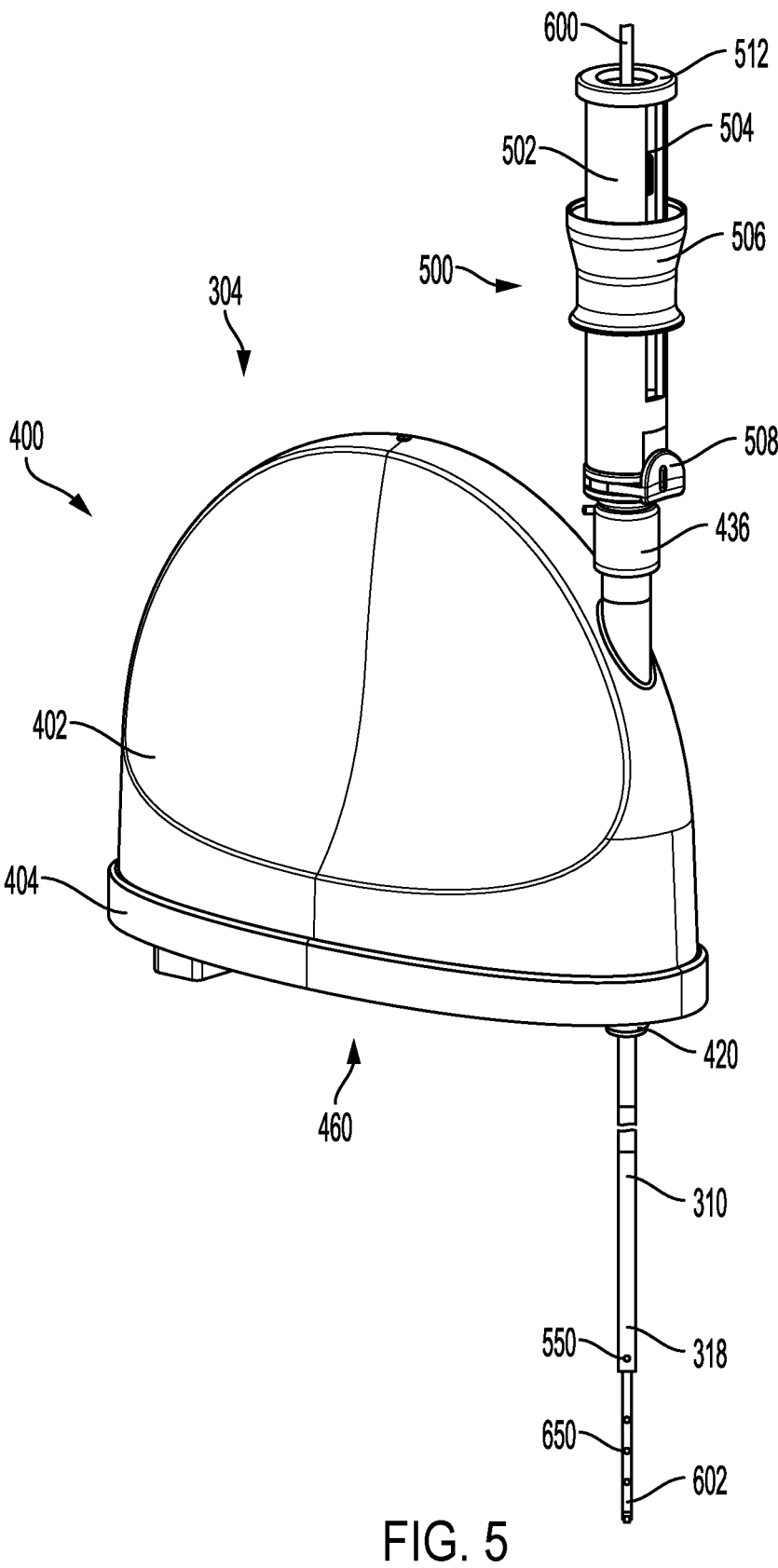
FIG. 5 illustrates a backend mechanism of a medical instrument system, in accordance with embodiments of the present disclosure.

FIGS. 4 and 5 are perspective views of a backend mechanism 304 independent of the instrument carriage 306 from FIGS. 3A and 3B, and including a flexible elongate device 310 extending distally from the backend mechanism 304. Referring to FIGS. 4 and 5, the backend mechanism 304 includes a housing 400, including a cover 402 and a chassis 404. The chassis 404 may be arranged to support components of the backend mechanism 304. In some embodiments, a flexible elongate device 310 may be axially fixed to the housing 400 of the backend mechanism. In some embodiments, the flexible elongate device 310 may be fixed within an opening of the chassis 404. In a non-limiting example, the chassis 404 may include a boss 420 to engage and retain the flexible elongate device 310, though other attachment arrangements are also contemplated.

As shown in FIGS. 4 and 5, the cover 402 may comprise a cavity that is sized and shaped to interface with the chassis 404 and to cover and protect the components carried by the chassis 404. The chassis 404 may include a mounting face 460 opposite the cover 402 arranged to interface with the instrument carriage 306 (see FIGS. 3A and 3B). In some implementations, the instrument carriage 306 may include drive mechanisms such as drive motors, which interface with and drive the components of the backend mechanism 304 and may include pin or other connectors that may provide an electrical communication interface that may interface with a printed circuit assembly, for example. Various components of the backend mechanism 304 are further described in U.S. patent application Ser. No. 17/047,414, which is incorporated by reference herein in its entirety.

As shown in FIGS. 4 and 5, in some embodiments, the cover 402 may comprise a protruding boss 436 extending in a direction opposite the opening of the cover. In this implementation, the protruding boss 436 comprises a passage providing access to a proximal portion of the flexible elongate device 310 and a proximal opening for a channel extending through the flexible elongate device 310. In some implementations, the cover 402 may serve as a handler gripping surface for the backend mechanism 304. Accordingly, it may be shaped and sized for convenient grasping by a human hand in some embodiments.

As shown in FIGS. 4 and 5, in some embodiments, the backend mechanism 304 may include a tool extender 500 that is mounted to the housing 400. In some embodiments, the tool extender 500 may include an elongated housing 502 having a channel 503 extending through the elongated housing (see FIG. 6). A distal end of the elongated housing 502 may be configured to attach to the protruding boss 436, or other appropriate portion, of the cover 402. The elongated housing 502 may be attached and secured to the protruding boss 436 using a fastener 508 or any appropriate type of connection (e.g., threads, snap-fit, adhesives, bonding, etc.) to maintain the elongated housing 502 of the tool extender axially and rotationally fixed relative to the backend mechanism 304. When attached, the channel 503 extending through the elongated housing 502 may connect to the passage of the protruding boss 436 providing access to a tool insertion port of the flexible elongate device 310 and a channel extending through the flexible elongate device 310. A proximal portion 319 of the elongate member 310 may be at least partially received in the channel 503 and extend distally out from a distal end of the elongated housing 502. The flexible elongate device 310 may be held stationary relative to the housing 400 and overall backend mechanism 304. Although the tool extender is shown in FIGS. 4 and 5 as being attached to the protruding boss 436, the tool extender 500 may be attached to any portion of the housing 400 of the backend mechanism 304 that provides access to the tool insertion port of the flexible elongate device 310. While the tool extenders disclosed herein are attached directly to a housing a backend mechanism, in some embodiments, a tool extender may be attached indirectly to a backend mechanism, including direct attachment to an insertion port of the flexible elongate device 310 and/or any other appropriate portion of a medical system.

As shown in FIGS. 4 and 5, a tool 600 may be inserted into an opening at a proximal end portion of the tool extender 500 and extend through the channel 503 of the elongated housing 502 and into a tool insertion port of the flexible elongate device 310. The tool 300 may be navigated through a channel of the flexible elongate device 310 until a distal end portion 602 of the tool 600 reaches a distal end portion 318 of the flexible elongate device 310.

In some embodiments, a tool extender 500 may include a slider 506 configured to move axially along at least a portion of a length of the elongated housing 502. The slider 506 may engage a portion of a shaft of the tool 600 to axially fix the tool 600 to the slider 506. In some embodiments, the slider 506 may retain the tool 600 in a center of the slider 506 and/or the slider 506 may be keyed to form a sliding interface between the slider 506 and the elongated housing 502 for concentric linear movement.

In some embodiments, the tool 600 may be axially fixed to the slider 506 via a fastener 510 to grip a portion of the tool shaft. The fastener 510 may be any appropriate fastener capable of engaging the tool 600, such as but not limited to, twist-compression adapters, compression fittings, valves (e.g., Tuohy borst valve), detents, clamps, twist-to-grip shaft adapters, snap-fits, elastic compression fittings, adjustable elastic compression fittings, and/or any other appropriate type of fastener.

In some embodiments, the slider 506 may include a portion disposed on an outer surface of elongated housing 502. This portion of the slider may have a generally cylindrical shape and be coaxially arranged with the elongated housing 502. In some embodiments, the slider 506 may not extend completely around the elongated housing 502 but may extend only partially around the elongated housing. The slider 506 may have an ergonomically contoured shape along its length (e.g., outer diameter decreases towards a middle portion of the slider along its length), providing an indented area to receive a user's fingers, thumb, and/or other portion of a user's hand. The user may grasp the elongated housing 502 with one or more fingers of the user's hand and simultaneously grasp the slider 506 with one or more other fingers to move the slider relative to the elongated housing. It should be noted that references to fingers herein may include reference to a thumb. The user may move the slider 506 axially along the elongated housing 502 by pressing the one or more fingers against the slider 506 and moving the one or more fingers axially along the elongated housing. The contoured shape of the slider may provide surfaces against which to exert a force to assist in moving the slider in an axial direction. The slider 506 may include any appropriate shape to allow one or more fingers to engage the slider and move the slider axially along the elongated housing. In some embodiments, the user may move the slider 506 using only frictional forces between the one or more fingers and the slider. In one example, the slider 506 may be gripped by a user's thumb and index finger of a hand while the user's palm and some or all of the other fingers of the hand hold the elongated housing 502, with movement of the thumb and index finger being used to move the slider 506 relative to the elongated housing 502.

When a user moves the slider 506 relative to the elongated housing 502 (e.g., axially along the length of the elongated housing), the tool 600 correspondingly moves relative to the elongated housing 502 and relative to the flexible elongate device 310. Accordingly, moving the slider 506 axially relative to the elongated housing 502 axially moves the tool 600 relative to the flexible elongate device 310. FIG. 4 shows the slider in a first position with the slider 506 positioned at a proximal end of the elongated housing 502. Although FIG. 4 shows a distal end 602 of the tool extending from a distal end 318 of the flexible elongate device, the tool 600 may be positioned entirely within the flexible elongate device 310 in the first position such that the distal end 602 of the tool is positioned proximal to the distal end 318 of the flexible elongate device 310 in a retracted position. FIG. 5 shows the slider 506 in a second position with the slider moved distally along the elongated housing 502. In this second position, the tool 600 has moved in a distal direction relative to the flexible elongate device 310 such that the distal end 602 of the tool 600 extends from the distal end 318 of the flexible elongate device in an extended position.

Because the tool 600 is axially fixed to the slider 506, an axial distance the slider 506 moves relative to the elongated housing 502 from the first position to the second position is equal to an axial distance the tool 600 moves relative to the flexible elongate device 310. Accordingly, a user can easily control and determine a length of the tool 600 extending from the distal end 318 of the flexible elongate device by knowing the initial position of the tool 600 relative to the flexible elongate device 310 and measuring the distance the slider 506 moves relative to the elongated housing 502. In some embodiments, the elongated housing 502 may include measurement indicators (e.g., a ruler or other length markings) on an outer surface to facilitate determination of a distance the slider 506 has moved. In some embodiments, one or more radiopaque markers may be attached to the distal ends of the flexible elongate device 310 and/or the tool 600 that are viewable to a user on a screen associated with an x-ray imager (e.g., using fluoroscopy, computed tomography (CT), cone beam CT (CBCT), etc.). In a non-limiting example, a radiopaque marker 550 may be positioned on a distal end portion 318 of the flexible elongate device 310 and a plurality of radiopaque markers 650 may be positioned at known intervals along a length of a distal end portion 602 of the tool 600. The user may view the radiopaque markers 550 and 650 on the screen to determine a distance the tool 600 extends from the distal end of the flexible elongate device 310 by viewing the radiopaque markers 650 of the tool relative to the radiopaque marker 550 of the flexible elongate device 310. In another example, a plurality of radiopaque markers may be positioned at known intervals along a length of the distal end portion 318 of the flexible elongate device 310 and a radiopaque marker may be positioned at the distal end portion 602 of the tool 600. A radiopaque marker may include a dedicated marker used to facilitate distance measurement or some other structure with radiopaque properties (e.g., and other functionality).

In some embodiments, the elongated housing 502 may include a slot 504 that extends at least partially along a length of the elongated housing 502. The slider 506 may be arranged to move axially along the elongated housing 502 within the slot 504. For example, as described in further detail below, a portion of the slider 506 may extend through the slot 504 to connect a portion of the slider disposed in the channel 503 of the elongated housing with a portion of the slider disposed on an outer surface of the elongated housing 502. As such, the slider 506 may move along a length of the slot 504 and the elongated housing 502. In some embodiments the slot 504 extends along only a portion of a length of the elongated housing 502 and constrains a maximum relative motion between the slider 506 and the elongated housing 502 between a fully retracted position and a fully extended position. The slot 504 also may prevent rotational motion of the slider 506 relative to the elongated housing 502, and thus may prevent rotational motion of the tool 600 relative to the flexible elongate device 310.

Figures 6A, 6B:
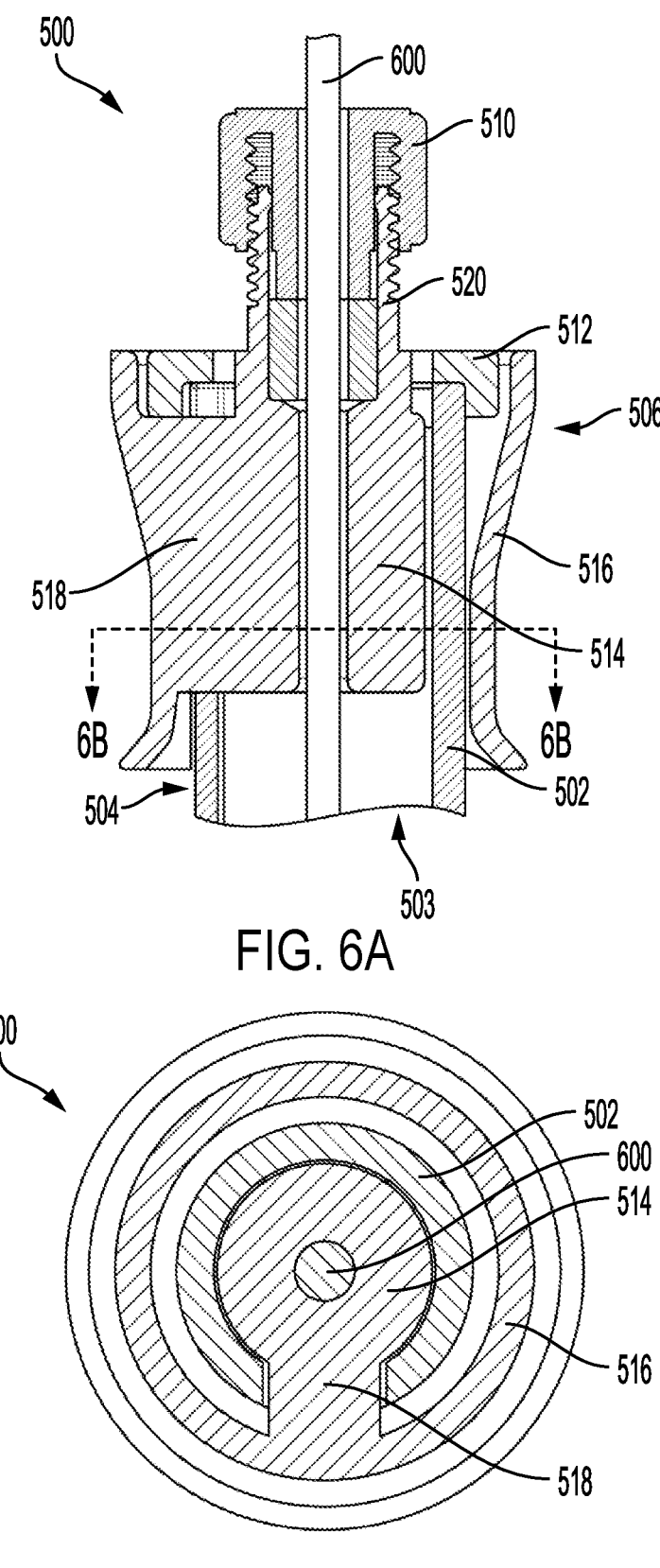
FIG. 6A illustrates a cross-sectional schematic of a tool extender of a backend mechanism, in accordance with embodiments of the present disclosure.
FIG. 6B illustrates a cross-sectional schematic of the tool extender at line 6B of FIG. 6A, in accordance with embodiments of the present disclosure.

FIG. 6A illustrates a cross-sectional schematic of a proximal portion of a tool extender 500 of a backend mechanism and FIG. 6B illustrates a cross-sectional schematic of the tool extender 500 at line 6B of FIG. 6A, in accordance with embodiments of the present disclosure. As shown in FIGS. 6A and 6B, a slider 504 is in a first position at a proximal end portion of the elongated housing 502. In some embodiments, the slider 506 includes a first portion 514 disposed in a channel 503 of the elongated housing 502 and a second portion 516 disposed on an external surface of the elongated housing 502. In some embodiments, the slider 506 has a longitudinal axis that is coaxial with the longitudinal axis of the elongated housing 502. The first portion 514 and the second portion 516 may be connected via a connector portion 518 that extends through and is retained in the slot 504 in a radial direction from the first portion 514 to the second portion 516 of the slider 506.

In some embodiments, the first portion 514 of the slider 506 may be configured to engage a shaft of the tool 600 positioned within the channel 503. As shown in FIG. 6A, the first portion 514 may include an extension 520 that extends proximally from the first portion 514 and includes an attachment mechanism for securing a portion of a shaft of the tool. In some embodiments, the extension 520 may include threads for receiving a twist-to-grip shaft adapter 510 that grips the tool shaft when threaded onto extension 520. However, any appropriate connection for axially fixing the tool 600 to the slider 506 may be used. When the tool 600 is fixed to the slider 506, a user may move the slider 506 relative to the elongated housing to correspondingly move the tool 600 relative to the elongated housing 502.

Figures 7A, 7B:
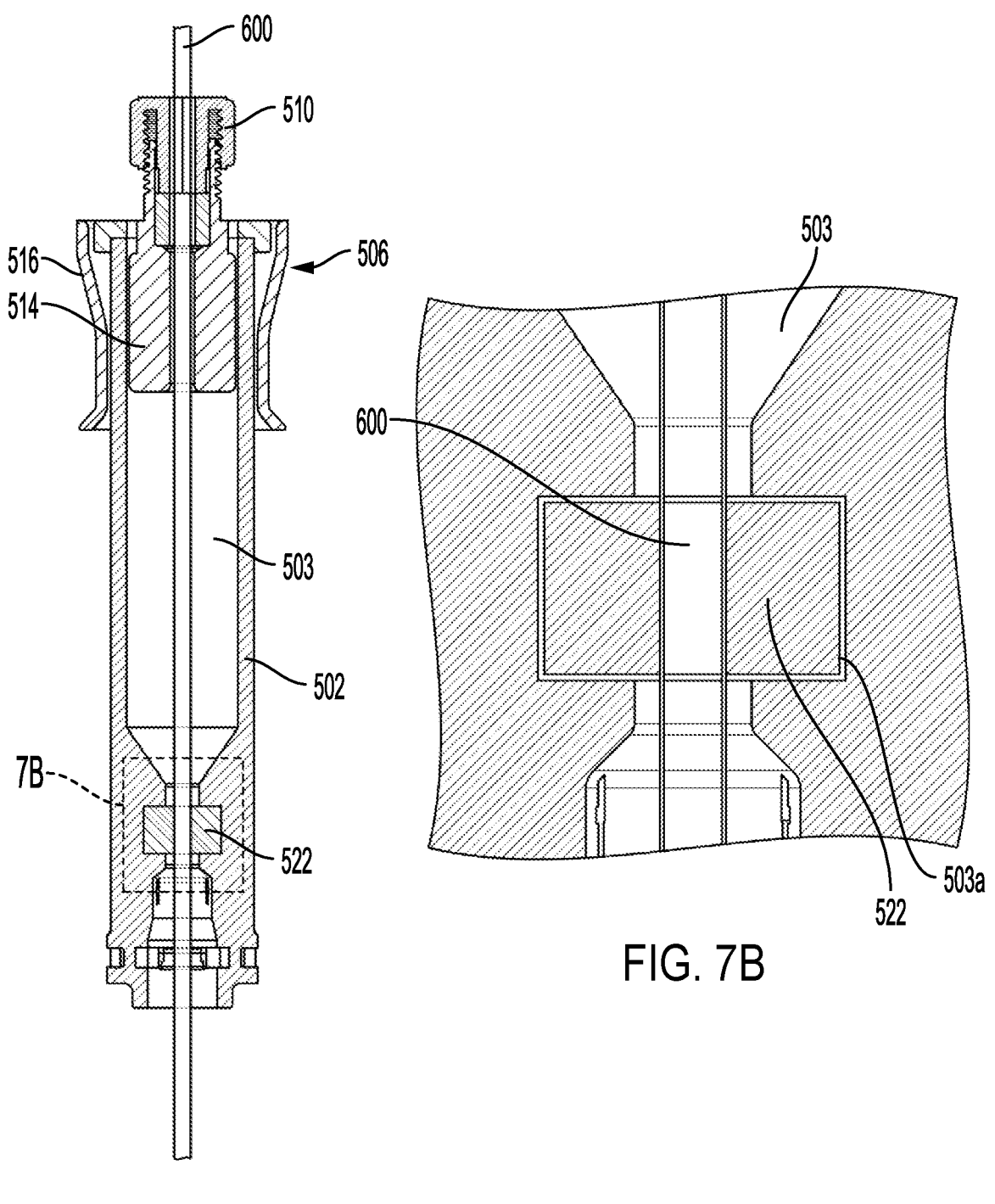
FIG. 7A illustrates a cross-sectional schematic of a tool extender of a backend mechanism, in accordance with embodiments of the present disclosure.
FIG. 7B illustrates an enlarged view of box 7B of FIG. 7A, in accordance with embodiments of the present disclosure.

FIGS. 7A and 7B illustrate a cross-sectional schematic of one embodiment of a tool extender 500, in accordance with embodiments of the present disclosure. In some embodiments, a position of the tool 600 relative to the elongated housing 502 and to the flexible elongate device 310 may be maintained due to friction between a shaft of the tool 600 and an inner wall of the flexible elongate device 310. In some embodiments, the tool extender 500 may include one or more elastic compression fittings 522 coupled to the elongated housing 502 and configured to apply a retention force to the shaft of the tool 600. The elastic compression fitting 522 may have a ring like, or other appropriate cylindrical shape with an appropriately sized and shaped hole extending therethrough and positioned in the channel 503 such that the compression fitting 522 is retained in a desired location along a length of the channel 503 and the tool extends through the through hole. For example, FIG. 7B illustrates the fitting 522 positioned and retained within a groove 503a formed on an interior surface of the channel 503. Thus, the compression fitting 522 may form a compression fit with the tool extending through the compression fitting 522. The compression fitting 522 may provide sufficient frictional force to retain the tool 600 stationary relative to the compressing fitting 522 and elongated body 502 absent a force applied by a user. Thus, the user may selectively move the tool 600 within the channel 503 using the slider 506 and maintain the position of the tool 600 when a user removes one or more fingers from the slider 506.

Figures 8A, 8B, 8C:
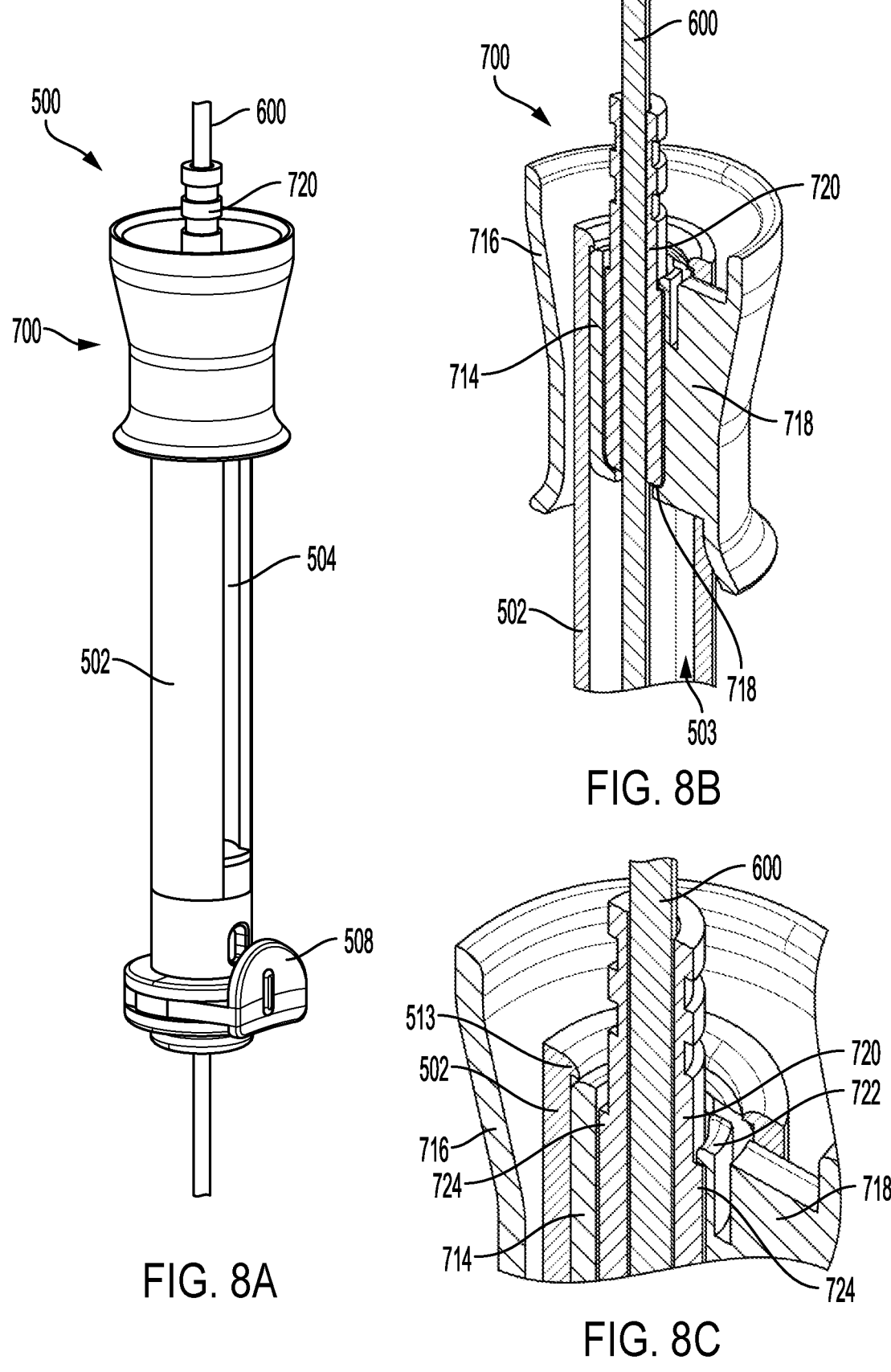
FIG. 8A illustrates a tool extender, in accordance with embodiments of the present disclosure.
FIG. 8B illustrates a cross-sectional schematic of the tool extender of FIG. 8A, in accordance with embodiments of the present disclosure.
FIG. 8C illustrates an enlarged portion of the tool extender of FIG. 8B, in accordance with embodiments of the present disclosure.

FIGS. 8A-8C illustrate an embodiment of a slider 700 that is configured to allow rotation of the tool 600 relative to a tool extender 500. For example, in some medical procedures, a user may need to rotate the tool 600 relative to a flexible elongate device, such as to reach a desired target area or otherwise control the movement of the tool 600. As shown in FIGS. 8B and 8C, a slider 700 may include an inner portion 714 disposed in a channel 503 of an elongated housing 502 of a tool extender 500. The slider 700 may also include a second portion 716 disposed on an outer surface of the elongated housing 502 and a connector portion 718 that connects the first and second portions through a slot 504 that is formed in and extends at least partially along a longitudinal length of the elongated housing 502 of the tool extender 500.

In some embodiments, the slider may include a sleeve 720 that may be attached to a portion of a shaft of the tool 600. The sleeve 720 may be attached to the tool shaft using any appropriate type of attachment (e.g., bonding, adhesive, compression fit, etc.) such that the tool shaft is axially fixed to the sleeve 720. The sleeve 720 may be configured to form a snap-fit, or other selective or rotatable connection, to a portion of the slider 700. In the depicted embodiment, the sleeve 720 may include a ridge 724 that is configured to engage with a detent 722 at the proximal end of the inner portion 714. The detent 722 may have an arm extending in a proximal direction with an inwardly extending ledge at a proximal end. When a user inserts the tool 600 with attached sleeve 720 into a proximal end of the tool extender 500, the sleeve 720 may deflect the detent radially outward until the ridge 724 passes the ledge on the detent such that the ledge engages the ridge 724 of the shaft 720. Depending on the construction of the illustrated connection, or other appropriate connection, the tool retained within the sleeve 720 may be rotated relative to the slider 700 as elaborated on below.

In some embodiments, as shown in FIG. 8B, the inner portion 714 may have an inwardly tapered ledge 718 at a distal end that conforms to the shape of the sleeve 720 such that the sleeve 720 is axially fixed to the slider 700 between the detent 722 and ledge 718. In this position, the sleeve 720 may rotate freely relative to the slider 700, allowing a user to rotate the tool 600 relative to the elongated housing 502 and to the flexible elongate device 310. Accordingly, the user may move the tool 600 in both axial and rotational directions. In some embodiments, a proximal end of the elongated housing 502 may have an inwardly extending ridge 513 to restrict movement of the slider 700 and prevent the slider 700 from being removed proximally from the elongated housing 502. In some embodiments, the sleeve 720 may be formed of silicone or an appropriate material. In some embodiments, the tool is rotationally locked relative to the slider of the tool extender and flexible elongate device, or the rotational movement of the tool may be locked or unlocked relative to the slider of the tool extender and flexible elongate device.

In some embodiments, the tool extender may be configured to retain a position of a slider relative to an elongated housing. For example, the slider may include a lock that selectively maintains the position of the slider relative to the elongated housing. This results in the longitudinal position of the tool being locked with respect to the flexible elongate device.

Figure 9C:
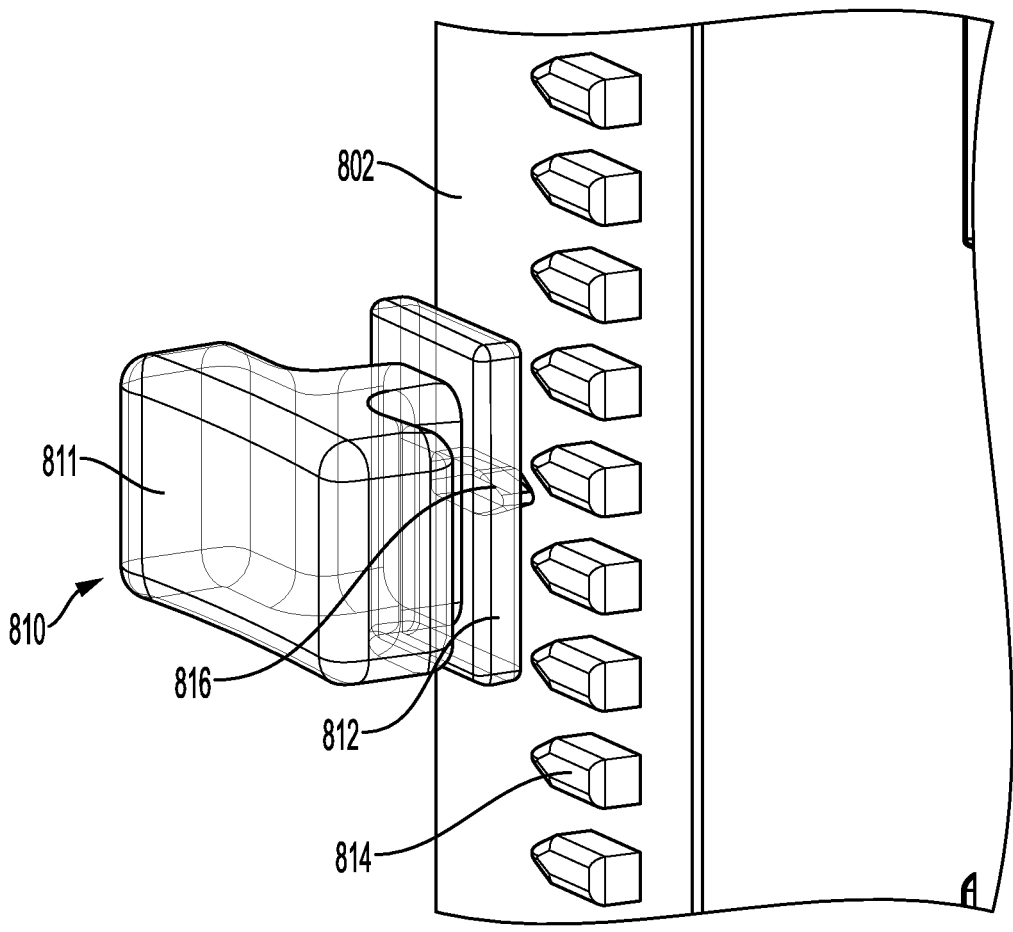
FIG. 9C illustrates the locking mechanism of the tool extender of FIG. 9A with the slider moved out of engagement, in accordance with embodiments of the present disclosure.

As shown in FIGS. 9A-9C, a tool extender 800 may include a slider 806, or other locking structure, disposed on an elongated housing 802 with a lock 810 to selectively maintain a position of the slider 806 with respect to the elongated housing 802. Specifically, the slider and lock may be operated to selectively prevent or permit movement of the slider 806 relative to the elongated housing 802 when the lock is moved between a locked and unlocked configuration. For example, the lock 810 may be moved between an unlocked configuration in which the slider may be moved axially along the elongated housing and a locked configuration in which the slider is axially fixed relative to the elongated housing. FIG. 9B shows the tool extender 800 with a portion of the slider 806 removed and FIG. 9C shows the tool extender 800 with the slider 806 removed to illustrate the lock 810. As shown in FIGS. 9B and 9C, the lock 810 may include an outer portion 811 disposed on an outer surface of the slider to receive a user's finger and an inner portion 812 disposed between the slider 806 and the elongated housing 802. An inner surface of the inner portion 812 may include a projection 816 that is configured to slide between a plurality of tabs 814 arranged along a longitudinal length of the outer surface of the elongated housing 802. The tabs are spaced apart from one another along a length of the device to allow the projection 816 to fit between two consecutive tabs 814. As shown in FIG. 9B, the projection 816 at least partially overlaps with the plurality of tabs 814 such that the inner surface of the inner portion 812 slides on top of the tabs 814 while the projection slides between the tabs. FIG. 9C shows the lock in an unlocked configuration with the projection 816 disengaged from the tabs 814. In this position the slider 806 may move axially relative to the elongated housing. When the lock 810 is moved laterally into the locked configuration, the projection 816 slides between two consecutive tabs 814, preventing the slider 806 from moving axially.

As shown in FIGS. 9A and 9B, the elongated housing 802 may include measurements 820 on an outer surface for a user to determine the distance the slider has moved relative to the elongated housing 802. Accordingly, the distance a tool engaged by the slider 806 has moved relative to a flexible elongate device may be easily determined by a user.

Figure 10:
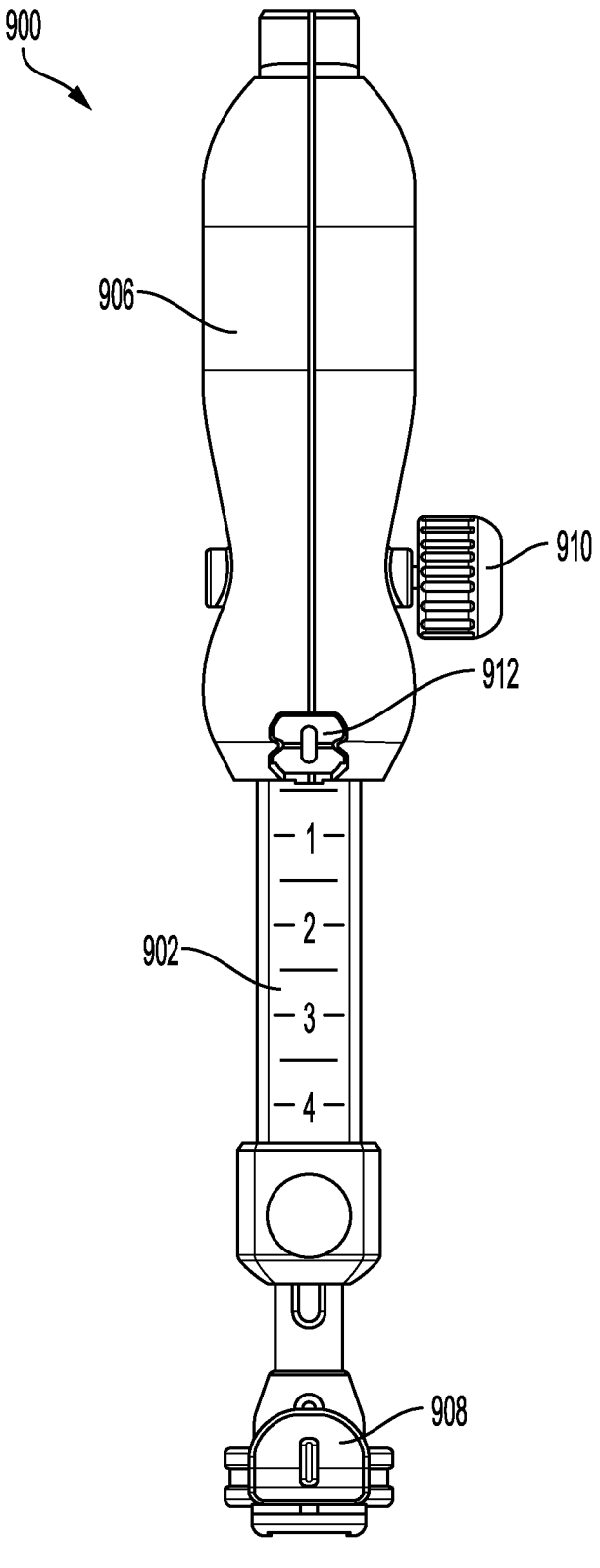
FIG. 10 illustrates a tool extender, in accordance with embodiments of the present disclosure.

FIG. 10 shows a tool extender 900 with a different lock 910 to selectively maintain the position of a slider 906 disposed on an elongated housing 902 of the tool extender 900. In this embodiment, the lock may include a knob that rotates in one direction to lock the slider 906 relative to the elongated housing 902 and rotates in an opposite direction to allow the slider 906 to move relative to the elongated housing 902 using a compression lock or other appropriate type of lock. Accordingly, it should be understood that the current disclosure is not limited to any particular type or construction of lock.

While the present teachings have been described in conjunction with various embodiments and examples, it is not intended that the present teachings be limited to such embodiments or examples. On the contrary, the present teachings encompass various alternatives, modifications, and equivalents, as will be appreciated by those of skill in the art. Accordingly, the foregoing description and drawings are by way of example only.

The invention claimed is:

1. A tool extender comprising:
an elongated housing including a channel extending through the elongated housing, and wherein the elongated housing is configured to be stationarily attached to a tool insertion port of a flexible elongate device;
a slot extending along at least a portion of a length of the elongated housing; and
a slider including a first portion disposed in the channel and a second portion disposed on an external surface of the elongated housing, wherein the first portion and the second portion of the slider are connected through the slot of the elongated housing, and wherein the first portion of the slider is configured to be engaged with a shaft of a tool positioned within the channel of the elongated housing to cause, by movement of the slider, a corresponding axial movement of the tool within and relative to the flexible elongate device.

2. The tool extender of claim 1, wherein moving the slider along the length of the elongated housing correspondingly moves the tool relative to the elongated housing.

3. The tool extender of claim 1, wherein the slider is configured to be axially fixed to the shaft of the tool.

4. The tool extender of claim 3, wherein the slider is engaged with the shaft of the tool via one of an elastic compression fitting and an adjustable elastic compression fitting.

5. The tool extender of claim 1, further comprising an elastic compression fitting coupled to the elongated housing and configured to apply a retention force to the shaft of the tool.

6. The tool extender of claim 1, wherein the slider extends at least partially around the elongated housing and is configured to be grasped by a user's hand.

7. The tool extender of claim 1, wherein the elongated housing is configured to be grasped by one or more fingers of a user's hand and the slider is configured to be grasped by one or more other fingers to move the slider relative to the elongated housing.

8. The tool extender of claim 1, further comprising a lock configured to maintain a position of the slider relative to the elongated housing when the lock is in a locked configuration.

9. The tool extender of claim 1, further comprising a sleeve arranged between the shaft of the tool and an internal surface of the slider, wherein the sleeve is configured to permit rotation of the slider relative to the shaft of the tool.

10. The tool extender of claim 1, wherein a longitudinal axis of the slider is aligned with a longitudinal axis of the elongated housing.

11. The tool extender of claim 1, wherein the flexible elongate device is a catheter or an endoscope.

12. The tool extender of claim 1, wherein the slot extends along only a portion of the length of the elongated housing and constrains maximum relative motion between the slider and the elongated housing.

13. The tool extender of claim 1, wherein the slot prevents relative rotational movement between the elongated housing and the slider.

14. The tool extender of claim 1, wherein the slot is enclosed by exterior surface of the elongated housing.

15. A method for controlling movement of a medical instrument, the method comprising:
positioning a tool in an elongated housing stationarily attached to a tool insertion port of a flexible elongate device, wherein the tool extends into a first channel extending through the flexible elongate device of a medical instrument;
retaining the tool in a slider that is slidingly disposed in a second channel extending through the elongated housing; and
moving the slider relative to the elongated housing while maintaining an axial position of the flexible elongate device relative to the elongated housing to axially move the tool within and relative to the flexible elongate device.

16. The method of claim 15, further comprising fixing the slider axially to a shaft of the tool.

17. The method of claim 16, further comprising engaging the slider with a shaft of the tool via one of an elastic compression fitting and an adjustable elastic compression fitting.

18. The method of claim 15, further comprising coupling an elastic compression fitting to the elongated housing to apply a retention force to a shaft of the tool.

19. A medical instrument comprising:
a flexible elongate device including a first channel extending through a flexible elongated body of the flexible elongate device;
a tool extender stationarily coupled to a tool insertion port of the flexible elongate device, the tool extender comprising:
an elongated housing having a second channel extending through the elongated housing,
a slot extending along at least a portion of a length of the elongated housing; and
a slider including a first portion disposed in the second channel and a second portion disposed on an external surface of the elongated housing, wherein the first portion and the second portion of the slider are connected through the slot of the elongated housing, and wherein the first portion of the slider is configured to be engaged with a shaft of a tool positioned within the second channel of the elongated housing and the first channel of the flexible elongate device to cause, by movement of the slider, a corresponding axial movement of the tool within and relative to the flexible elongate device.

20. The medical instrument of claim 19, wherein moving the slider along the length of the elongated housing correspondingly moves the tool relative to the elongated housing.

\* \* \* \* \*